United States Patent [19]
Stadler et al.

[11] Patent Number: 5,286,634
[45] Date of Patent: Feb. 15, 1994

[54] SYNERGISTIC METHOD FOR HOST CELL TRANSFORMATION

[76] Inventors: Joan K. Stadler, 3313 Oakland St., Ames, Iowa 50010; Nunzio M. Antonelli, via Pezze del Sole, 24, Bari, Italy, 70125

[21] Appl. No.: 414,091

[22] Filed: Sep. 28, 1989

[51] Int. Cl.$^5$ .............................................. C12N 15/00
[52] U.S. Cl. .............................. 435/172.3; 435/172.2; 435/240.4; 435/317.1
[58] Field of Search ............... 435/172.3, 172.2, 240.4, 435/317.1

[56] References Cited

PUBLICATIONS

Theodore M. Klein, et al., "Transfer of Foreign Genes into Intact Maize Cells with High-Velocity Microprojectiles", *Proc. Natl. Acad. Sci. USA*, 85, p. 4305 (1988).
Petrukhina, et al., "The Regulation of Liposome Permeability by Polyelectroylyte", *J. Controlled Release*, 3, (1986) 137–141.
Felgner et al. (1987) Proceeding Nat. Acad. Sci. vol. 84, pp. 7413–7417.
Petrukhina et al. (1986) J. Controlled Release vol. 3 (2–3) pp. 137–142.
Steinbliss et al. (1983) International Review of Cytology Supplement 16, pp. 191–208.

*Primary Examiner*—Gary Benzion
*Attorney, Agent, or Firm*—Lerner, David, Littenberg, Krumholz & Mentlik

[57] ABSTRACT

This invention addresses the problem of inserting foreign or nonative DNA into a cell and, most particularly, into a plant cell. The solution to this problem of DNA transfer set forth in this invention is the use of a polycationic compound and cationic liposomes which act synergistically to accomplish host cell transformation.

13 Claims, 9 Drawing Sheets

Eco RV

SYNERGISTIC METHOD FOR HOST CELL TRANSFORMATION

FIELD OF INVENTION

This invention relates to the field of molecular biology and, in particular, the field of genetic engineering. More particularly, this invention relates to protocols for transfection of cells. Most particularly, the invention describes a new and highly efficient transformation protocol.

BACKGROUND OF THE INVENTION

Much excitement has been generated in the technical, scientific and lay communities about the potential benefits arising from the developments of genetic engineering technology. Most frequently, public attention and praise are focused on the pharmacological and public health benefits associated with genetic engineering. Examples of the genetically engineered pharmaceutical products that have been given kudos include genetically engineered tissue plasminogen activator and, more recently, erythropoietin.

It is understandable that these pharmaceutical and public health related achievements have garnered much of the public attention surrounding genetic engineering. However, application of genetic engineering technology to nonpharmaceutical related areas holds the same excitement and promise as application of genetic engineering technology to the public health sector. In particular, the application of genetic engineering tools to agricultural products, both plant and animal, holds out the exciting prospect of disease and pest resistant animals and plants. In this connection, great energies have been spent in these fields as well as public health fields to perfect or optimize the genetic engineering methods used by scientists to create these beneficial fruits of genetically engineered products.

This invention is not the type of genetically engineered discovery that appears on the front pages of newspapers, on the radio or on television. The "sex appeal" that is required to achieve such notoriety is not a part of this invention. Rather, this invention is principally directed to the methodology of genetic engineering. It is envisioned that the application of the methodology taught by this invention will someday result in the creation of a genetically engineered plant, animal or drug that will achieve the type of notoriety which results in extensive media coverage.

Many lay individuals who otherwise understand and, indeed, marvel at the benefits genetic engineering holds for society, do not fully appreciate the high degree of technical skill required to establish a scientific methodology or protocol that permits the actual genetic manipulation of cells. At the most basic level, genetic engineering is the transfer or movement of the "chemical blueprint" of cells, as encoded in nucleic acids, from one cell in which such a chemical blueprint naturally occurs to another cell, called the host cell, that does not naturally contain the chemical blueprint. It is important that this transfer occur in such a way that the host cell can accurately read and express the chemical blueprint even though the blueprint is not its own.

One of the many technical difficulties of genetic engineering is to find a way to move the chemical blueprint, called deoxyribonucleic acid (DNA), from the cell in which it naturally occurs into the host cell. This problem of DNA movement required to transfect or transform a host cell is particularly acute in the case of plant host cell transformation, although the problem is certainly also prevalent in the transformation of other cellular life forms.

Various methodologies have been introduced into the genetic engineering field to facilitate this transfer of DNA from one cell to another. Included in such transfer technologies are the methods of electroporation, high velocity microprojectiles, polyethylene glycol (PEG) transformation, calcium phosphate, microinjection and Aqrobacterium-mediated transformation. Problems, particularly with DNA transformation of cells especially plant cells and most especially monocot plant cells such as corn (maize), are extant with all these methodologies.

For example, electroporation is many times an inefficient and highly costly methodology. Although electroporation is a reliable procedure, it results in pronounced loss of cell viability (3, 7) caused by, among other factors, destruction of the cell membrane and/or of cell wall integrity. Microprojectiles are cumbersome to use, costly and, as their name implies, damaging to cell membranes and/or cell walls causing significant loss of cell viability by virtue of the fact that a bullet-like projectile is being "shot" into the host cell. Aorobacterium-mediated DNA transformation is a painstaking process. In addition, it is not useful for monocot plant species generally because certain species are not susceptible to infection or transformation by Aqrobacterium bacteria, a step necessary for subsequent DNA transfer. The PEG methodology for host cell transfection is an extremely difficult methodology over which a genetic engineering researcher has somewhat minimal control and this methodology is highly toxic to cells generally. In addition to the difficulties associated with the aforementioned methodologies, all DNA transformation techniques must address the problem of introducing foreign DNA into a host cell so that the foreign DNA manifests some significant stability in the host cell thereby achieving the ultimate aim of genetic transformation—to stably express the transformed DNA chemical in a host cell. This is referred to as stable transformation of the host.

Achieving stable host transformation is a problem that extends across all forms of cellular life. However, the problem is especially acute in plant cells. Unlike animal cells that have no cell walls, plant cells have cellulosic cell walls. It is a characteristic of these cell walls that they are very difficult to penetrate. Accordingly, transformation of plant cells has proved more difficult than transformation of other cells because scientists attempting to transform nonplant cells need not deal with the complex problems of moving DNA across the cellulosic plant cell wall. Thus, it is easier to move DNA into an animal cell than a plant cell. Scientists have surmounted this problem by modifying plant cells so that the cellulosic cell wall is removed providing direct access to the plant cell membrane. (Because animal cells lack cell walls, membranes form the outer boundary of animal cells.) Plant cells lacking cell walls are termed protoplasts or naked cells. Because the cell wall is removed from these plant cells, the ability to transform such cells with nonnative DNA is increased. In most cases, the cell walls regenerate in 6-24 hours.

The achievement of stable transformation is a relative criterion that is principally a function of the time in which foreign DNA is inside a host cell and in which the host cell maintains the ability to express the transformed DNA. In plants and in animals such stable transformation is best achieved by methods which lead to the incorporation of the foreign DNA into chromosomes. However, stable integration especially in animal cells can be achieved with certain vectors that replicate freely in animal cells without integration into chromosomes. Until stable transformation is achieved, the transformation is said to be transient. Obviously, any host cell that has been stably transformed has passed through a stage at which it could only be said that the host cell was transiently transformed. However, it must be appreciated that transient transformation of a cell (and transient expression of the transformed DNA) is not a guarantor that stable transformation will occur. Among the reasons for this is the relative unpredictability of biological systems.

The transformation technique of this invention is a simple and elegant protocol that uses two common, relatively inexpensive "off-the-shelf" chemicals in a combined or coordinated manner such that a synergistic effect between the two chemicals results as manifest by extremely efficient DNA transformation in all cells, most notably in plant cells and especially notably in monocot plant cells. Indeed, the two chemicals that are combined by this invention, a polycation compound and a cationic liposome compound, have been used individually to effect DNA transformation. Although other researchers have combined DNA transformation methodologies in the past, in particular combining the techniques of PEG and electroporation (29), the reports of the alleged success of this latter combination have been dubiously received by the scientific community. Regardless of that, the combination of the present invention results in a very efficient transformation, significantly greater than the PEG and electroporation combination even assuming that such a combination is effective. Thus, this invention teaches a methodology termed 2PC that permits transient and stable transformation of host cells.

This invention employs two common chemicals used in an extremely simple methodology that does not require sophisticated machinery or great expense. Accordingly, this invention has great application for all genetic engineering laboratory undertakings, whether in highly sophisticated molecular biology research labs such as are extant in major universities and corporations throughout the world, or whether in simple laboratory settings such as in a high school biology laboratory.

It is therefore an object of the present invention to provide a method for transforming a host cell. More particularly, it is an object of this invention to provide a method for transformation of plant cells, especially monocot plant cells.

It is a further object of this invention to provide a method of cell transformation that is applicable to all cells and that employs relatively low technology means thus providing for the use of this technology by a broad spectrum of laboratories.

It is a still further object of this invention to provide for transformed cells that have been transformed by the synergistic action of a polycation compound and a cationic liposome to effect both transient and stable transformation of the host cell.

SUMMARY OF THE INVENTION

This invention addresses the problem of inserting foreign or nonnative DNA into a cell and, most particularly, into a plant cell. The solution to this problem of DNA transfer set forth in this invention is the use of a polycationic compound and cationic liposomes which act synergistically to accomplish host cell transformation.

According to this invention, a recombinant cell can be made comprising nonnative and native DNA in which the nonnative DNA is introduced into the cell by the coordinated use of a polycation compound and a cationic liposome compound during transfection of the cell thereby transforming the cell. Any type of cellular life form can be so transformed although the invention is most efficient when used with a cell lacking a cell wall, that is, a cell having an outer boundary that is a membrane. Types of cells having a membrane as an outer boundary include mammalian cells and protoplasts of either monocotyledonous or dicotyledonous plant cells.

Transformation of cells according to this invention is accomplished by treating a host cell for a predetermined time with a solution of a polycation compound thus forming a cell polycation complex. DNA nonnative to the host cell is treated with a suspension of cationic liposomes to form a DNA liposome complex. Thereafter the cell polycation complex and the DNA liposome complex are combined giving rise to a synergistic effect that transforms the host cell with nonnative DNA.

 Control.

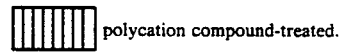 polycation compound-treated.

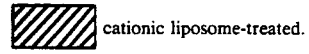 cationic liposome-treated.

 2PC treated.

Figure 5:
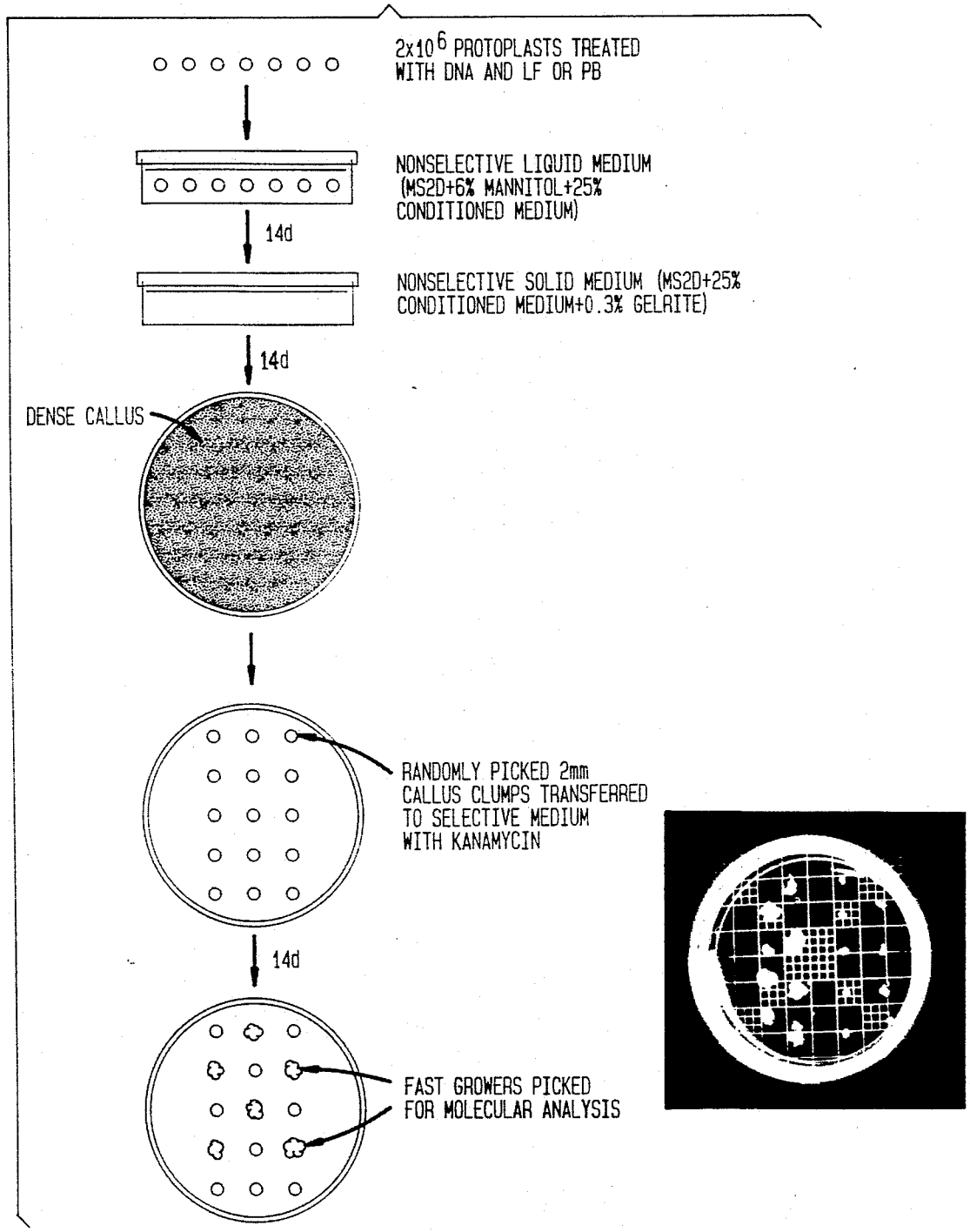

FIG. 5. Method for selection of stable Kan® transformants after pCaMVNeo transfection. Inset shows fast-growing BMS-M transformants after 7 d on medium with 200 ug/ml kanamycin.

Figure 6:

FIG. 6. Integration of nptII in genomic DNA of two independently selected Kan® transformants obtained by 2PC transfection. Genomic DNAs were digested with EcoRV and probed with the BamHI nptII fragment of pCaMVNeo. EcoRV enzyme cuts at one EcoRV site within the CaMV promoter of the donor DNA (or cassette), and also cuts at EcoRV sites at different positions in maize DNA adjacent to the site of insertion of the donor DNA, thus revealing the integration of donor DNA in the transfected host cell. Lanes: a, DNA from nontransformed BMS-M; b, DNA from BMS-M stably transformed with pCaMVNeo by the PEG method; c,d, DNA from two stable BMS-M Kan® transformants after transfection with pCaMVNeo by the 2PC method.

Figure 7:
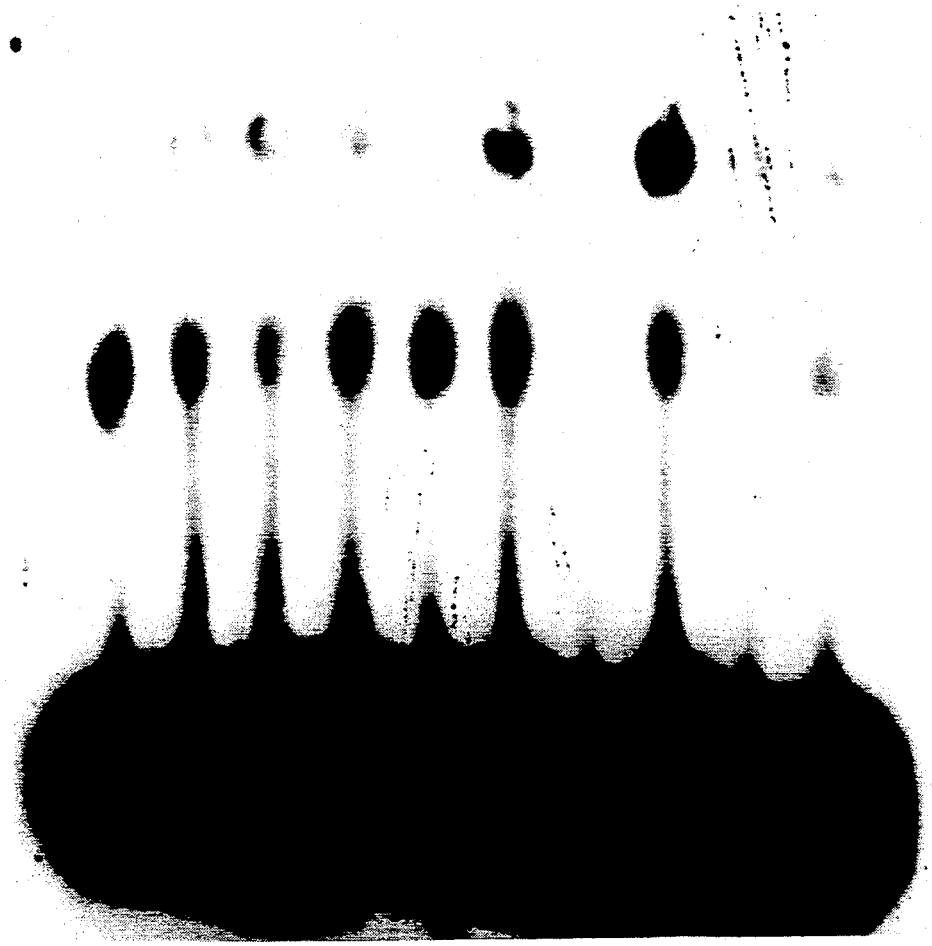

FIG. 7. Phosphorylation of kanamycin by nptII genes integrated into BMS-M following 2PC transfection. The reaction products were separated on TLC plates and detected by autoradiography. Lanes: 1 and 5, BMS-M control; 2,3 and 4, BMS-M transformed with nptII., phosporylated Kanamycin.

Figure 8:
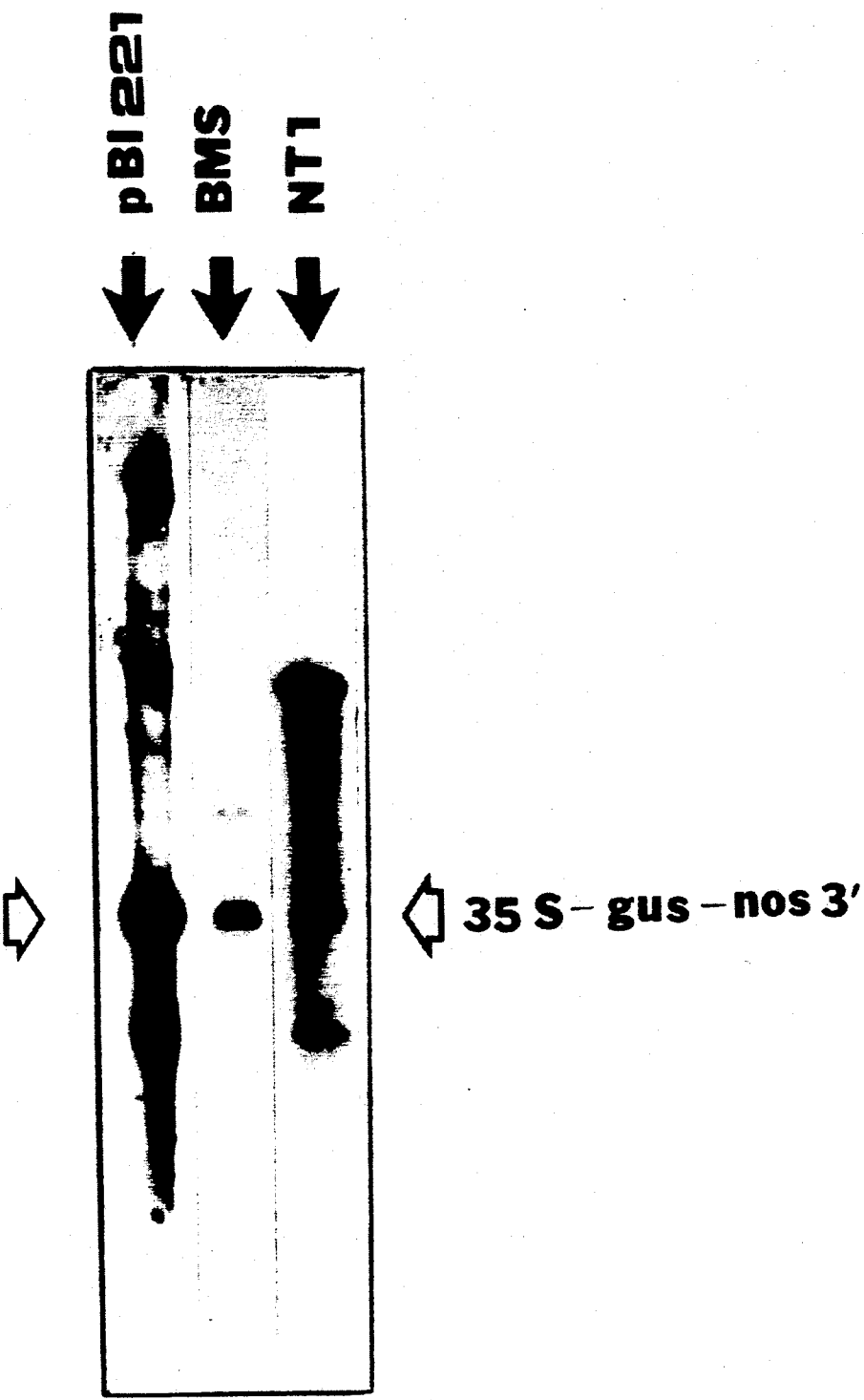

FIG. 8. Integration of the GUS gene in BMS-M (maize) and NTI (tobacco) stable transformants after transfection of pZA50 by 2PC methods. Genomic DNAs probed with a PstI, EcoRI fragment from pZA50 containing CaMV35S, the GUS structure gene, and nos 3'. Lanes: pBI221, the parent plasmid used in pZA50 construction and containing the same PstI EcoRI fragment; BMS, stable 2PC-mediated maize transformant; NTI, stable 2PC-mediated GUS transformant in tobacco.

Figure 9:
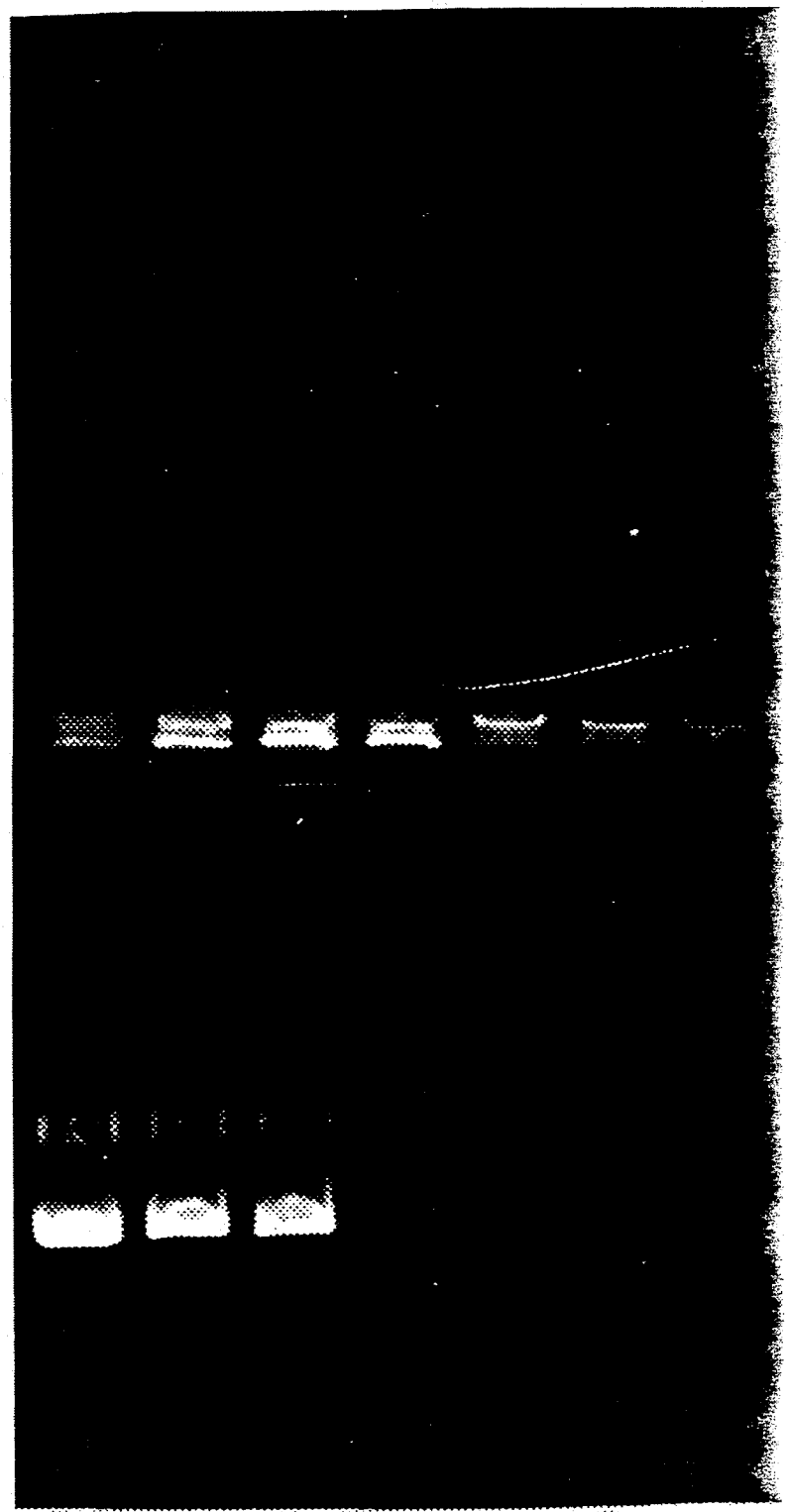

FIG. 9. Electrophoresis of plasmid DNA previously mixed with varying quantities of cationic liposome. For each sample in lanes 2–4, 2 ug of pZA50 was reacted with the following concentrations of cationic liposome to give the indicated DNA:cationic liposome ratios in parentheses. Lanes: 2, 2 ul cationic liposome (1:1); 3,5 ul cationic liposome (1:2.5); 4, 10 ul cationic liposome (1:5). Samples in lanes 5, 6, and 7 had 2 ug pZA50 plus 2, 5, and 10 ul cationic liposome respectively, plus 30 ug polycation compound each. Lane 1 contains only 2 ug plasmid DNA.

DETAILED DESCRIPTION OF THE INVENTION

The recombinant cells and recombinant methodologies disclosed herein provide for highly efficient transformation of cells. This invention represents an advance over the known methods of transformation by virtue of the demonstrated effectiveness of the methodologies and by the established application of the methodologies to regenerable cell lines.

Many of the procedures associated with practicing the non-inventive steps of the protocol needed to practice this invention have been elucidated and are set forth in publications available in scientific libraries and the like. The more pertinent publications are listed in the Bibliography annexed hereto. In these instances, the publications are identified using a numerical code system in which each reference listed in the Bibliography is identified by a unique arabic numeral. All the references listed in the Bibliography or otherwise identified herein are hereby incorporated by reference.

Using the techniques of this invention, transient and stable activity of nonnative genes in host cells has been demonstrated. In particular, such activity has been shown in plant cells derived from both monocotyledonous and dicotyledonous plants. Transformation of cells from other kingdoms including animal cells using this methodology are also achievable.

This invention exploits the known properties of two relatively simple and inexpensive chemicals. In particular, the invention sets forth that these two chemicals, a polycation compound and cationic liposomes, can be used in a coordinated fashion to significantly increase the likelihood of obtaining transformed cells. As noted, use of polycation compounds and cationic liposomes individually for cellular transformation is known but heretofore no one has combined these two compounds to obtain the highly successful transformation obtained by this invention.

The methodology of this invention has been generally designated 2PC or dual polycation. The 2PC transfection protocol involves the coordination or combination of two chemicals, a polycationic compound and cationic liposomes. Using the methodology of this invention, the host cells or protoplasts derived therefrom are treated with a polycationic compound and the foreign DNA to be introduced into the host is exposed to cationic liposomes. The DNA cationic liposome complex resulting therefrom is then contacted with the host cell polycationic complex. Evidently, this invention is a strikingly simple and elegant protocol. In view of this, the 2PC method is believed to be a highly desirable alternative to other known transfection protocols such as electroporation or polyethylene glycol. The 2PC method also provides a higher degree of transformed cell viability than other known methods.

The underlying theoretical mechanism of the 2PC protocol is not well understood although the results of practicing the protocol are well established as set forth herein. This invention exploits the discovery that a synergistic interaction advantageously effecting host cell transformation occurs between the polycation compound and the cationic liposomes. A possible hypothesis explaining this invention is extant and is set forth below. However, it will be appreciated that regardless of the ultimate accuracy of this hypothesis, the methodology disclosed herein for effecting efficient cellular transformation is not affected by the accuracy of this hypothesis.

It is currently believed that foreign or nonnative DNA is introduced into a host cell using the teachings of this invention when a synergistic reaction occurs by virtue of charge interaction arising from the described treatment of the transfecting DNA and pretreatment of the host cell with polycation. This interaction of charges leading to DNA transfer occurs because of the attraction of charges on aggregates, (formed by previous exposure of DNA to a suspension of cationic liposomes) to the charges present on host cells following host cell pretreatment with a polycation compound. In particular, it is the current hypothesis that following treatment of the correct ratio of foreign DNA to a cationic liposome suspension, the DNA adheres to the outside of the aggregate formed from the interaction of the treated DNA and the liposomes.

The putatively, negatively charged foreign DNA complexes or aggregates are believed to be attracted to the plasmalemma of the host cell following host cell treatment with a polycation compound which changes at least part of the overall charge of the host cell from negative to positive resulting in attractive forces between the putatively, negatively charged DNA aggregates and the putatively, positively charged host cell. It will, of course, be understood that the foregoing is merely a hypothesis and that the success of the 2PC method is no doubt dependent on numerous complex physiological processes. A fuller discussion of the theory explaining the 2PC methodology is set forth below under the appropriately entitled subheading.

Prior to discussing particular preferred embodiments of this invention, a general discussion of the methodologies involved in the invention and the host cells upon which this methodology can be practiced is set forth. These discussions are grouped by subheading to facilitate understanding of this invention.

Host Cells

This invention is applicable to all cellular life forms. The application of the methodology disclosed herein is believed to be most applicable to animal cells generally and mammalian cells in particular, and plant cells especially plant cells of the subtype protoplasts. The reason for this belief is discussed in part in the Background Of The Invention section in which the problems associated with known transfection protocols is set forth.

Any cell can be used with this invention. As set forth in FIG. 8, this invention is exemplified herein through use of monocotyledonous and dicotyledonous cells. In particular, the maize and tobacco plants which exemplify monocot and dicot plants respectively were used. In all instances, stable transformation of host cells was achieved. Also, animal cells such as mammalian cells as exemplified by Chinese hamster ovary (CHO), mouse embryo 3T3, or human diploid fibroblast cells can be used. It will be understood by one skilled in the art that certain modifications of this protocol, all within the skill of the ordinary practitioner, will have to be made depending on the particular cell being transformed. By way of example, the media used during the transformation process will have to change for each type of cell so that the media is compatible with the particular cell line to be transformed. Among the reasons such media compatibility is required is to maintain the proper osmolality for cells in a particular medium. Examples of the different types of media that can be used include MS or N6 media for corn; NT1 media for tobacco; and for CHO cells, a medium comprising alpha medium and 10% fetal calf serum (10).

The Polycation Compound

The use of polycationic compounds to help effect transformation of cells is known (8,30). In particular, use of the polycation compound, hexadimethrine bromide sold under the brand POLYBRENE or other salts of hexadimethrine is known. Also, use of polycationic compounds such as the salts of poly-L-ornithine or other salts of polyamines have been known to facilitate inoculation of protoplasts with viruses (28). Other examples of polycations or salts of polyamines that could be used in the 2PC method of this invention are salts of poly-L-arginine, poly-L-lysine, poly-D-lysine, polyallylamine and polyethleneimine. In addition, any polycationic compound prepared from the combination of any compound containing at least two good leaving groups, such as dihalogenated compounds especially dibromide and diiodide but less desirably difluoride, or ditosylates and any poly(tetraalkyl-substituted amine) containing chains of two or more carbons between the amine groups could also serve as an effective polycationic compound for this invention. In the instance of the salt of hexadimethrine, the compound containing two good leaving groups could be 1,3 dibromopropane and the poly(tetraalkyl substituted amine) is N,N,N',N'-tetramethylhexamethylene diamine. In this case, the polyamine is a diamine. Indeed, almost any combination of alkyl or xylyl groups attached to a basic carbon chain and combined using the aforementioned good leaving groups would be effective polycations. However, for reasons regarding weakening the basicity of the compound, it is believed that aryl groups attached directly to nitrogen compounds would be less effective than the foregoing compounds.

Other compounds that behave in a fashion similar to polycationic compounds can also be used. For example, polyglycols such as polyethylene glycol or polypropylene glycol solutions in a mixture with a mannitol solution containing calcium ions would be effective as a substitute for a polycationic compound. Other inert sugars other than mannitol could be used to adjust osmoticum. Indeed, any polyglycol would likely work in this context and any divalent cation such as magnesium could be substituted for the divalent cation calcium.

Cationic Liposomes

The cationic liposomes of this invention are prepared by methods well known in the art (10) and are available commercially, for instance under the name LIPOFECTIN. Cationic liposome compounds comprise a suspension of cationic liposomes, which are vesicles comprising an artificial lipid bilayer. The cationic liposomes can be constructed by any known means such as the means set forth in the aforementioned reference or, as noted, by purchasing such cationic liposomes commercially.

Theoretical Hypothesis

The protocol for transfection with 2PC is straightforward, uses easily available chemicals and requires no expensive equipment. Using both maize and tobacco it has been shown that the 2PC method promotes transformation in both monocots and dicots.

The precise mechanism of interaction of polycationic compound and cationic liposomes in promoting the 2PC synergistic response is not understood. However, it is known from use of cationic liposomes alone for DNA transformation that cationic aggregates were produced when DNA was mixed with the cationic liposomes in a ratio of 1:5. It was thus proposed that these positively charged aggregates would fuse with negatively charged cell membranes (10). It is believed that if the concentration of DNA relative to cationic liposomes was increased, negatively charged aggregates carrying a large amount of DNA would probably be produced because the increased number of DNA molecules used should adhere as efficiently to the outside as to the inside of a group of the cationic liposomes. Then, the putative negatively charged DNA complexes should subsequently be attracted to plasmalemma which has been treated with polycation to change at least some of the overall charge from negative to positive. Success of the 2PC method is probably dependent on several complex physiological processes, but data is extant to support the aforementioned theory.

Transfection of maize protoplasts by cationic liposomes alone was most successful when 0.1 or 0.5 ug DNA was complexed with 25 ug cationic liposome (DNA/lipid ratios of 1:250 or 1:50) and most erratic when DNA/lipid ratios were 1:2.5, 1:1.25 or 2:1 when 10, 20 or 50 ug DNA was used. These observations are consistent with the hypothesis that the former aggregates should have been largely positive, and that the latter (according to the instant hypothesis) could have been largely negative and less efficiently attracted to the plasmalemma. The 2PC method was most successful when cationic liposomes were complexed with 10 or 20 ug DNA (DNA/lipid ratios of 1:2.5 or 1:1.25) suggesting that the observed efficiency of transfection was due to the expected interactions of negatively charged cationic liposome DNA complexes with a positively charged polycation coated protoplast membrane. When applying the 2PC method of this invention to other cells, for example embryogenic maize, or to large DNA molecules, it is desirable to adjust the DNA/lipid ratio in a predetermined manner to facilitate such applications as exemplified by maximizing the amount of DNA as compared to the amount of lipid in the DNA/lipid ratio.

When one concentration of DNA (2ug) is complexed with cationic liposomes in ratios of 1:1, 1:2.5 and 1:5 and then electrophoresed for 3 h in a 0.3% gel, different patterns of migration are seen (FIG. 9 lanes 2, 3 and 4). The DNA control migrates as expected toward the positive electrode, the 1:1 and 1:2.5 mixed aggregates migrate like the control (although some material stays at the origin), and the 1:5 mixture stays entirely in the originating well. This indicates that the former complexes may be negative as predicted, while the latter are positive as proposed (10).

When 30 ug polycation compound is added to these various DNA/cationic liposome mixtures, no migration is seen at all and the complexes are precipitated at origin (FIG. 9 lanes 5, 6 and 7). This finding suggests that a second mechanism might be involved in the interaction of the 2PC method, i.e., the precipitation of negatively charged DNA complexes onto the polycation coated surface of the plasma membrane.

DESCRIPTION OF PREFERRED EMBODIMENTS

Cells

A maize Black Mexican Sweet suspension culture, BMS-M, was used to exemplify application of the 2PC method. BMS-M cells were maintained in medium containing MS salts (11) supplemented with $(1^{-1})$ 2 mg 2,4-D, 0.5 mg thiamine, 20 g sucrose, 150 mg asparagine, and 250 mg glucose (MS2D)(12). Suspension cultures were routinely subcultured at 7 d intervals (0.004 g per ml initial inoculum) and grown with shaking at 150 rpm in the dark at 28° C. Under these conditions, cell populations were always in exponential growth between 2 and 6 d after inoculation. Population doubling time (Td), determined by increments in fresh weight, was usually 24 to 36 h.

Maize embryogenic callus lines were derived from immature $F_1$ embryos from crosses of inbred A188 X Mutator ($Mu^2$) lines. Cultures of 9- to 12-day embryos (approximately 1 to 2 mm in length) were initiated by standard methods(13) on N6(14) basal medium supplemented with 20 g sucrose, 0.74 mg/liter 2,4-D, 6 mM asparagine, 5.5 mM myoinositol, 12 mM proline, and 0.3% Gelrite. One month after culture initiation, the proline concentration was reduced to 6 mM. Cultures were incubated at 28° C. in the dark. After two weeks all embryos were moved without selection to fresh medium. Type II embryogenic callus was thereafter selected and propagated biweekly.

Protoplast Isolation

For application of the 2PC method to plant cell transfection protocols, transfection using protoplasts is recommended to facilitate DNA movement into the host. Ideally, the protoplasts selected should be capable of regenerating plants.

BMS-M cultures in log phase growth were harvested 4 d after transfer. Growth medium was decanted and the cells were plasmolyzed for 30 min at 25 rpm in MS2D with 8% mannitol (MS2D8M). Protoplasts were then isolated by known methods (12). Approximately 0.5 g fresh weight callus was incubated with mixing at 25 rpm at 28° C. for 4 h in 20 ml 2% cellulase and 0.25% pectinase dissolved in 80 mM calcium chloride, 0.2 M mannitol, pH 5.0. After incubation in enzyme mixture, the protoplast preparation was gently filtered first through a 70-um nylon mesh screen and subsequently through three 46-um nylon mesh screens. Enzymes were removed from the protoplasts by two 20 ml washes with MS2D6M. Cells were collected by centrifugation (50×g for 5 min) and resuspended in 5 ml MS2D6M for gene transfer. Protoplast viability after filtration and washing was tested by staining with fluorescein diacetate (15) and ranged from 75% to 95%. Contamination of the protoplast preparation with whole cells was determined using extant methodology (16). No intact cells remain after this treatment.

Protoplasts from A188/$Mu^2$ (a cell line known to regenerate plants) were prepared from callus tissue by existing methodology (17) and washed in N6 with 8% mannitol (N68M).

Plasmid DNA

Three transforming plasmids were used: pCaM-VI$_1$CN (18) containing the cauliflower mosaic virus (CaMV) 35S promoter, an Adh1 derived intron (I$_1$), the chloramphenicol acetyl transferase (CAT) coding sequence, and nos 3'; pCaMVNeo (7) containing the 35S promoter, the neomycin phosphotransferase gene (npt II) from Tn5, and nos 3'; and pZA50 (19), containing the 35S promoter, the B-glucuronidase (GUS) coding sequence and nos 3'. Plasmid DNA was prepared by standard methods (20). Any other marker cassette or cassette capable of expression in the target host cell can be used for transformation.

Probes to detect integration of transfected genes into host DNA include a 1.0 kb BamHI fragment containing nptII structural regions from pCaMVneo and a PstI EcoRI fragment from pZA50 containing 35S GUS nos 3' sequences. The isolated fragments were labeled with $^{32}P$ and a nick translation kit.

Transfection of Cells by Polycation Pretreatment Alone

After the final wash, protoplasts were resuspended in MS2D6M. Stock solutions of the polycationic compound hexadimethrine bromide sold under the brand POLYBRENE were freshly prepared for each experiment. The concentration of hexadimethrine bromide in these stock solutions was 10 mg/ml in phosphate buffered saline, pH 7.0, but any concentration compatible with the solubility properties of hexadimethrine bromide (or other polycation) would have been satisfactory. The final volume of each transfection mixture was 1.0 ml and contained 2×10$^6$ protoplasts in 0.5 ml MS2D6M, 30 ug of the polycationic compound in 0.1 ml MS2D6M, and the desired concentration of DNA in 0.4 ml MS2D6M. The diluted polycationic compound solution was added to the protoplast suspension, mixed gently, and then transferred to a holding means such as a petri dish. The DNA suspension was then added slowly, most preferably by a dropwise methodology, into the polycation protoplast suspension. This cell-polycation-DNA mixture was placed on a gyro rotary shaker platform at 25 rpm for 15 min and then incubated without shaking at 28° C. for 6 h. After the 6 h incubation, the mixture was diluted by adding 4.0 ml MS2D6M and incubated further at 28° C. either for assay of transient gene expression or selection of stable transformants.

Transfection of Cells by Cationic Liposome Pretreatment of DNA Alone

Cationic liposomes in suspension were obtained commercially under the brand LIPOFECTIN (1 mg liposomes/1 ml). Protoplasts ($2 \times 10^6$ in 0.9 ml MS2D6M) were moved to a 60 mm petri dish. Transfecting DNA was prepared by adding 50 ul of a 1:1 dilution of cationic liposome stock suspension in water to 50 ul (desired concentration) DNA in water. This cationic liposome-DNA mixture (final concentration 25 ug cationic liposome plus DNA in 0.1 ml) was then incubated for 15 min at room temperature to allow the formation of lipid/DNA complexes. The cationic liposome DNA aggregate mixture was added dropwise to the protoplasts. The final protoplast-cationic liposome-DNA mixture was then rotated at 25 rpm for 15 min and incubated for 6 h at 28° C. before dilution with 4.0 ml MS2D6M.

Transfection of BMS-M Cells by 2PC

This method combines pretreatment of the recipient cells by polycation compound and pretreatment of the transfecting DNA with cationic liposomes. Protoplasts ($2 \times 10^6$ in 0.5 ml MS2D6M) were pretreated as set forth with 30 ug of the polycation compound in 0.1 ml medium for not more than approximately twelve hours or for not less than approximately one minute but most preferably for approximately fifteen minutes. Treatment of animal cells including mammalian cells can be for as long as twenty-four hours. DNA-cationic liposome aggregates or complexes were produced as set forth by addition of 50 ul of the desired concentration of DNA in water to 50 ul of a cationic liposomes suspension (previously prepared by making a 1:1 dilution of a cationic liposomes stock suspension with water) and subsequent incubation for 15 min at room temperature. An additional 0.3 ml water was then combined with the DNA cationic liposome complex and it was then added, preferably slowly, and most preferably dropwise, to the polycation treated protoplasts which had previously been placed in a holding means. The protoplast polycationcationic liposome-DNA mixture was rotated for 15 min at 25 rpm, incubated for 6-12 h at 28° C., and diluted with 4.0 ml MS2D6M.

Transfection of A188/Mu² Protoplasts by 2PC

Methods were identical to those described for BMS-M except that the growth medium with mannitol used at every step was N68M rather than MS2D6M.

The resultant transfection mixture containing either the A188/Mu² or the BMS-M protoplasts are jointly and individually referred to as a diluted transfection mixture for sake of simplicity in further elaboration of the protocol of this invention as set forth hereinafter.

Selection For Stable Transformants

After transfection treatment of BMS-M protoplasts the diluted transfection mixture was incubated without shaking at 28° C. in sealed holding vessels such as petri dishes for 14 d. Small clusters of dividing cells, the dividing microclusters, were then recovered by gentle resuspension, for instance using a rubber policeman, and centrifuged preferably at $50 \times g$ for 5 min. Part, approximately 1 ml, of the supernatant was removed, leaving a remaining volume of 4.0 ml. Four petri dishes were then prepared, each with 1 ml of this suspension plated on nonselective MS2D solid medium containing 0.3% Gelrite and 25% conditioned medium (CM) (12). CM was previously prepared for addition to Gelrite medium by filtration of the supernatant of BMS-M cells in logarithmic growth through 5-u, 0.45-u and 0.22-u membrane filters just before use. After 7 d, well-developed 2-mm microcalli were randomly picked and transferred to selective MS2D, 0.3% Gelrite plates containing 200 ug/ml kanamycin. These were incubated further at 28° C. for 7-14 d. Faster growing microcalli were then picked for further subculture and preparation of genomic DNA for use in Southern blot analysis.

Chloramphenicol Acetyl Transferase (CAT) Assays

Transfected protoplasts were incubated for 40 h before assay for CAT activity (21). Silica gel thin layer chromatography (TLC) plates were exposed to X-ray film for 18 h at room temperature. Protein concentration was determined by the Bradford method (22).

Neomycin Phosphotransferase Assay

Neomycin phosphotransferase activity in selected kanomycin-resistant stable transformants was tested by the method of Cabanes-Bastos et al. (23).

Genomic DNA Isolation and Southern Blot Analysis

Genomic DNA was isolated from microcalli by a miniprep method (24). Restriction enzymes in particular BamHI, EcoRV, EcoRI and PstI were used for genomic DNA digestion as is well known in the art for such enzymes. Approximately 5 ug of high molecular weight DNA was digested with 3 to 5 units of restriction enzymes per ug DNA and subjected to electrophoresis through 0.8% agarose gels. UV-nicked DNA fragments were transferred to a nylon transfer membrane such as a Genetran membrane by the procedure of Southern (25) for 48 h. After baking for 2 h at 80° C. under vacuum, hybridizations were carried out in 50% formamide, $5 \times$ Denhardt's, $3 \times$ SSC, 100 ug/ml denatured salmon sperm DNA, 1% SDS, 5% dextran sulfate, and $2 \times 10^7$ cpm $^{32}$P-labelled DNA at 42° C. for 36 h. Filters were washed in 50% formamide, $5 \times$ SSC, 0.2% SDS for 30 min at 42° C., then washed two times for 20 min each in $2 \times$ SSC, 0.1% SDS, and two times in $0.1 \times$ SSC, 0.1% SDS. The first three washes were performed with agitation at room temperature and the last at 65° C. Filters were finally exposed at −70° C. for 1-2 d to Kodak XAR-5 film with an intensifying screen such as the lightening plus brand. Filters were prepared for rehybridization by removal of probe with 3 to 4 washings at 95° C. in $0.1 \times$ SSC, 0.1% SDS.

Transient Gene Expression in BMS-M Protoplasts After 2PC Transfection

Figure 1:
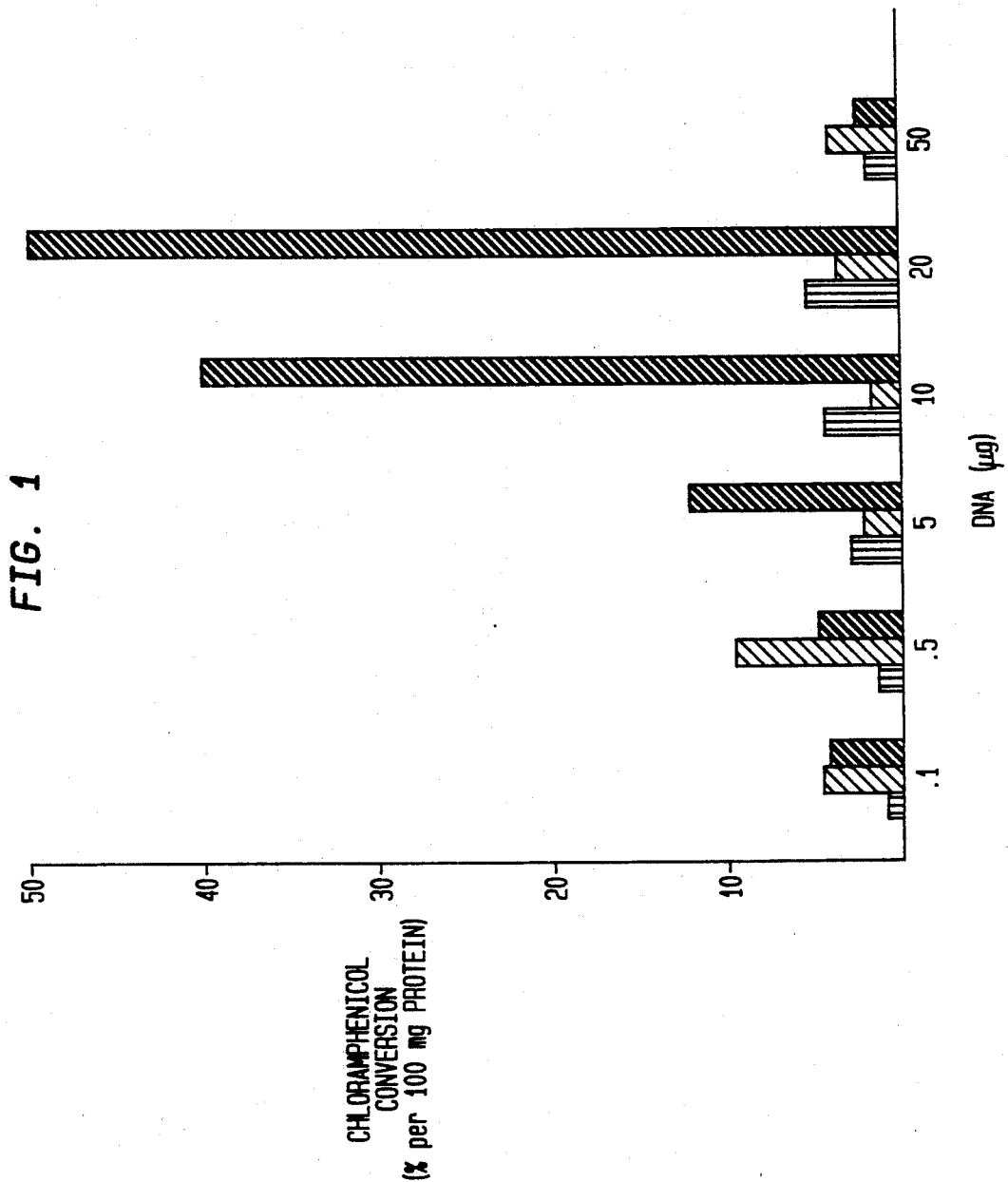
FIG. 1. CAT activity after transfection of BMS-M with cationic methods. Enzyme activity is expressed as % conversion of $^{14}C$ chloramphenicol to monoacetylated forms per 100 mg protein  polycation compound-treated protoplasts,  cationic liposome-treated protoplasts,  2PC- protoplast.
Figure 2:
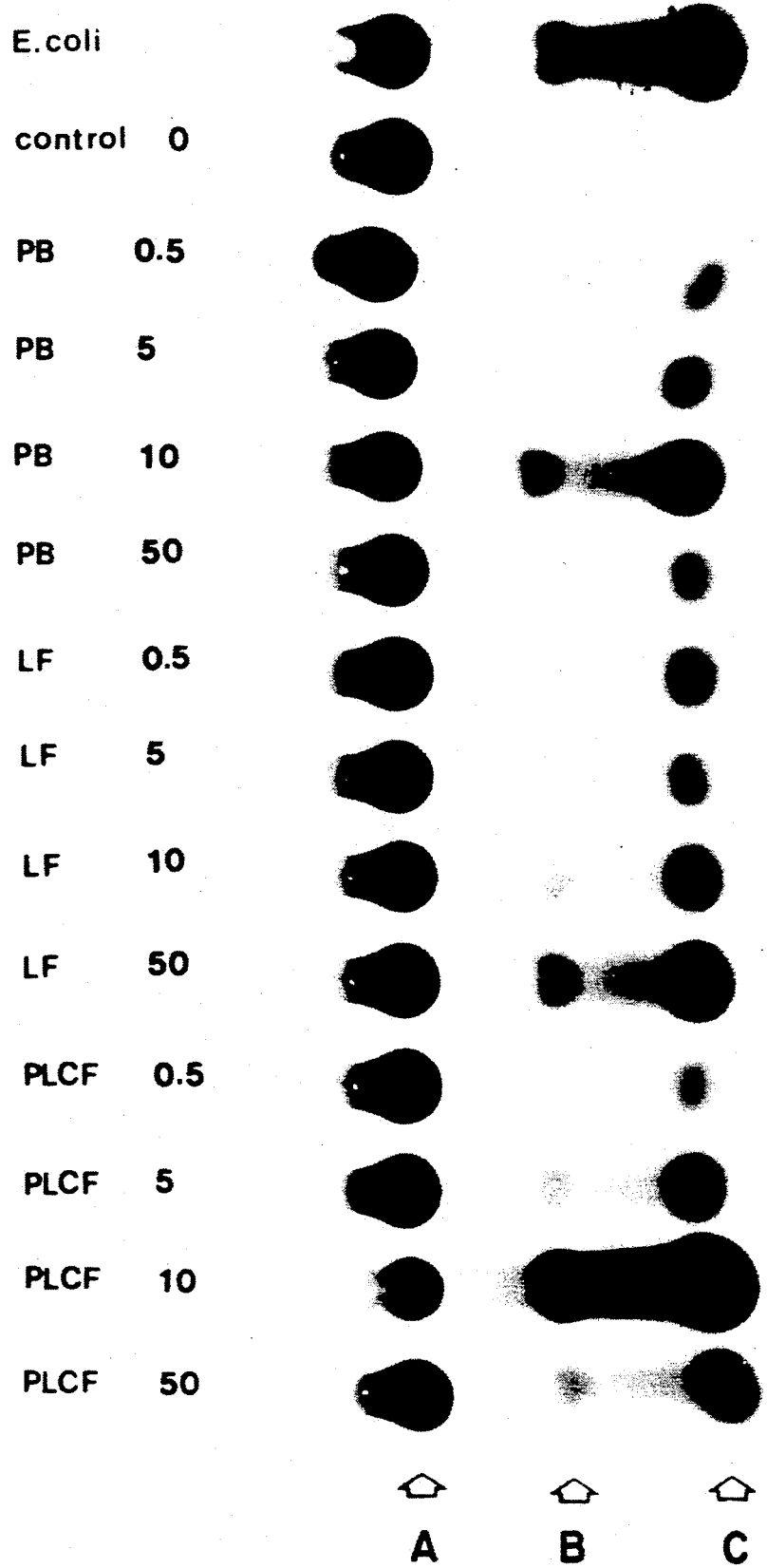
FIG. 2. Autoradiogram of a thin layer chromatography (TLC) plate showing acetylated products of 14C chloramphenicol after transfection of BMS-M with varying DNA concentrations by polycation compound, cationic liposome or 2PC methods. A, unreacted $^{14}C$ chloramphenicol; B, 1-acetylchloramphenicol; C, 3-acetyl chloramphenicol. PLCF, also termed 2PC.

Transient activity of the CAT reporter gene indicates successful plasmid DNA transfer and gene expression. CAT gene activity (% of $^{14}C$ chloramphenicol converted to acetylated forms) was determined after incubating BMS-M protoplasts for 40 h after transfection with the 2PC method. This CAT gene activity was compared to other prior art cationic transfection treatments, namely, use of cationic liposomes alone, specifically, use of the cationic liposome brand LIPOFECTIN and a polycation compound treatment alone, specifically, use of the polycation compound brand POLYBRENE. In each experiment, the CAT gene activity was compared with that in control samples with cation-treated cells but with no added DNA. For all 3 cationic methods good transient CAT expression was obtained over a wide range of DNA concentrations (FIGS. 1 and 2 and Tables 1 and 2.) FIG. 1 and Table 1 show that after polycation compound treatment CAT activity increases from 1 to 6% with increasing concentrations of transfecting DNA up to 20 ug. On the other hand, cationic liposome treated cells express CAT activity at all DNA concentrations from 0.1 ug to 50 ug. Transient CAT gene expression seen after plasmid transfer with 2PC is also dependent upon DNA concentration and varies from 2 to 49% per 100 mg protein (FIG. 1, Table 1) or from 8 to 65% when total sample proteins (Table 2) are assayed. Clearly, CAT activity obtained from cells treated with the 2PC method is markedly superior to the other cationic treatments used alone. An autoradiogram of a TLC plate showing CAT activity in one experiment after polycation compound, cationic liposome or 2PC treatment is shown in FIG. 2.

Synergistic Effect with 2PC Transformation

Using 2PC resulted in an increase in transient gene expression (Tables 1 and 2) when compared to methodology known in the prior art. Published theories (8, 10) of polycation compounds alone and cationic liposome action alone in the transformation of host cells failed to indicate that any synergistic effect would be extant between these two chemicals.

The data in Table 2 which is derived from values of CAT expression in total crude lysates of $2 \times 10^6$ protoplasts in each treatment sample shows that observed CAT activities after cellular transformation with 2PC range from 37 to 65% using 5-50 ug DNA which is treated with cationic liposome and transfected into cells treated with a polycationic compound. The expected additive values obtained after polycationic compound plus cationic liposome treatment would have been 10 to 13% and the increased synergistic effect of the 2PC methodology of this invention was a startling 3.6 to 5.1-fold increase over the expected values. Later, when total protein concentrations of treated protoplast samples were measured at the time of CAT assay, it was found that the amount of protein varied between samples and usually ranged from 150 to 250 mg. This sampling error probably evidences the difficulty of making accurate dilutions of protoplasts suspended in medium and loss of tissue in preparation of the crude cell lysate. Therefore, in subsequent experiments (Table 1) all CAT activity was expressed as a function of protein quantity. Again, a synergistic effect of combined or coordinated treatment with polycation and cationic liposome is seen in Table 1 when transfecting DNA concentrations are 5-20 ug. In this instance, the multiplicative increase is 2- to 5-fold over the expected additive effects of the polycation and cationic liposome treatments.

The amount of transfecting DNA used affects the reliability of expression using the 2PC invention as well as degree of synergism arising from the 2PC methodology. Synergistically elevated transient expression of the CAT genes was seen in 11/11 trials when 10-20 ug DNA was transfected. However, when other concentrations of transfecting DNA were used (0.1, 0.5 or 50 ug) only 6/13 trials showed the 2PC effect.

Figure 3:
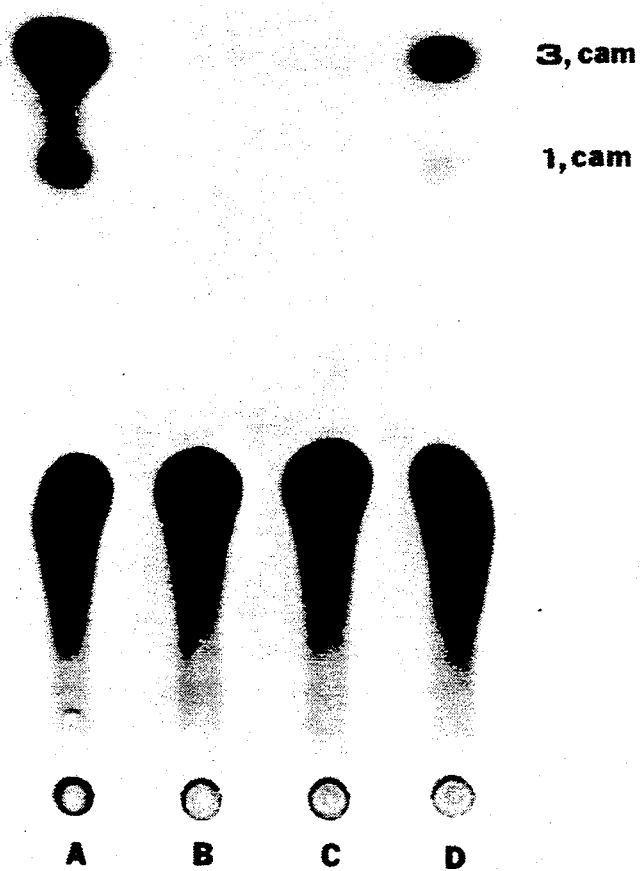
FIG. 3. Autoradiogram of TLC plate showing CAT gene expression after 2PC transfection of A188/Mu$^2$ protoplasts with 20 ug pCaMVI,CN. Lanes: 1, E. coli standard; 2, BMS-M untreated protoplasts plus DNA; 3, BMS-M protoplasts treated with cationic liposome and DNA; 4, BMS-M protoplasts transfected by 2PC and DNA.

The 2PC method is clearly more effective in promoting transformation measured by transient gene activity than polycation compound or the cationic liposome methods used alone. Stable transformants occurred in up to 40% of unselected colonies after 2PC treatment; transformants occurred in only 3-8% of colonies after polycation or cationic liposome treatment alone. This finding is also manifest by results obtained in experiments testing CAT gene transfer to protoplasts derived directly from A188/$Mu^2$ $F_1$ embryogenic maize callus. In these tests (Table 3 and FIG. 3) neither polycation nor cationic liposome methods (using $2 \times 10^6$ protoplasts and 20 ug DNA) promote significant, detectable gene transfer. 2PC, however, gave positive results and the measured CAT activity at 40 h was 1.4 to 10.8%. Expectedly, protoplasts derived from cultures in logarithmic growth are more transformation competent by polycation compounds and cationic liposome methods than protoplasts derived from cultures in lag phase. Apparently, the observed increased efficiency of the 2PC methodology has succeeded in overcoming this defect, so that even slowly dividing or nondividing cells can be transformed. The callus mass of A188/$Mu^2F_1$ embryogenic cultures enlarges 3-4 fold in 2 weeks, but BMS cells in culture have a 24-36 h doubling time.

The efficiency of the 2PC method was compared with direct gene transfer by electroporation, a noncationic method that uses protoplasts. In this comparison, electroporation ($3 \times 10^6$ protoplasts, 150 V and 800 uF of 10 ug quantities of DNA) usually yields 10-20% conversion of $^{14}C$ chloramphenicol. 2PC mediated transfection with 10 ug DNA produces an average value of 71% conversion for $2 \times 10^6$ treated protoplasts.

Protoplast Viability After Cationic Treatments Is Extraordinarily High

Figure 4:
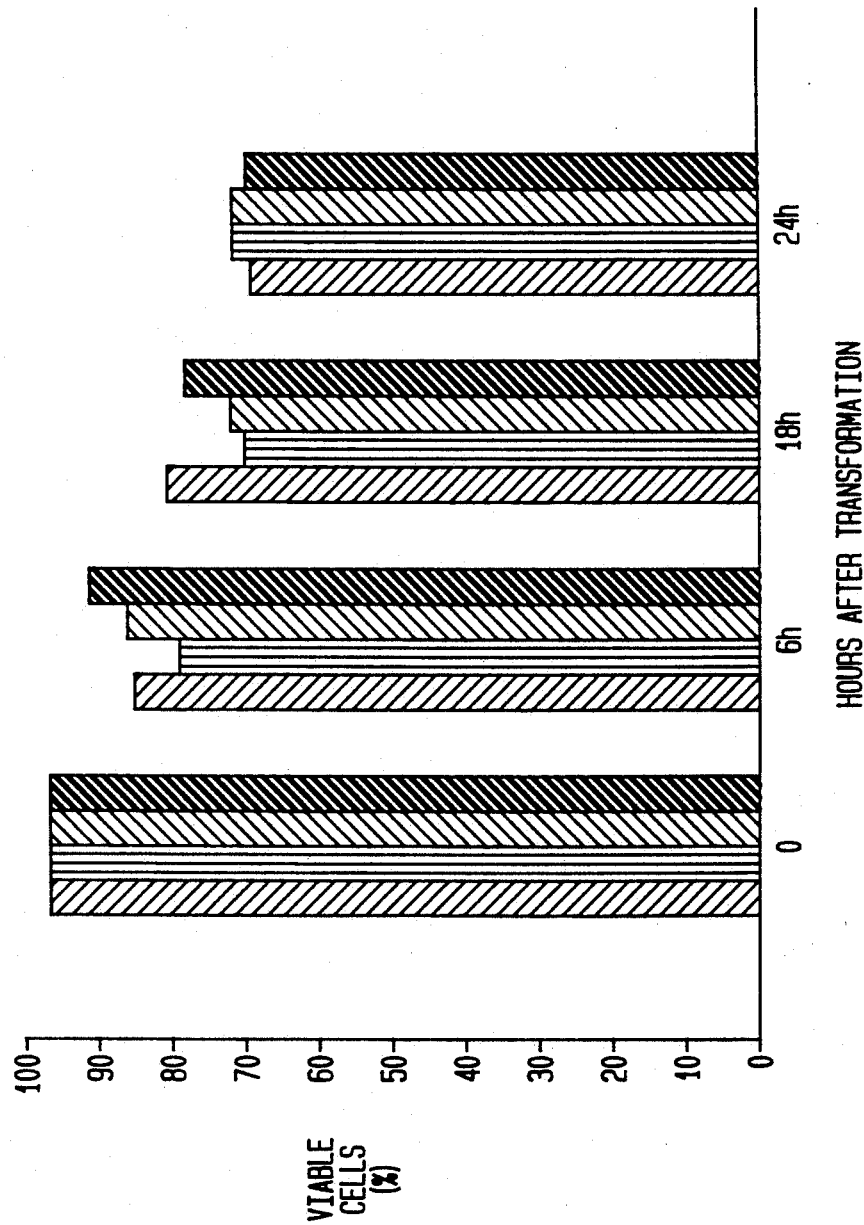
FIG. 4. Viability of BMS-M protoplasts after transfection by cationic methods.

Percentage of viable cells at 0, 6, 12 and 24 h after transfection was estimated by the fluorescein diacetate method (15) (FIG. 4). Data represented in this histogram show that neither polycation compound, cationic liposome nor 2PC treatments cause cytotoxicity. The number of viable cells is in all instances 100% of control values for untreated protoplasts at the four time points checked. The unprecedented lack of cell damage caused by transfection with these techniques may occur because cationic methods for gene transfer probably exploit the natural processes of plasmalemma fusion and endocytosis (10,8). Lack of cytotoxicity might also play a role in the above mentioned superior effectiveness of 2PC methods compared with electroporation. By comparison use of electroporation can and oftentimes does cause a 30 to 50% drop in viability of transfected protoplasts by 24 h (8) and often causes a lower yield of recovered protein in sample lysates, which implies cell loss.

Stable BMS-M Transformants Were Obtained By 2PC Transfection

Stable integration of transfecting DNA may occur after introduction to host cells using 2PC methodology. This requires that the entire transforming cassette (the structural gene and the attached regulatory components) reach the host nuclei in an undegraded form and that the cassette will remain undegraded until they are integrated into the new host genome. Further, expression of integrated transforming genes is necessary for the phenotypic recognition of stable genetically altered transformants. This second event is dependent upon successful molecular recombination of the entire transforming gene, including both structural and regulatory components, into a region of host DNA which will allow these sequences to remain unmethylated. It is evident that this invention allows for recovery of stable transformants after transfection by 2PC methodology of at least two different genes: nptII in pCaMVNeo and B-glucuronidase (GUS) in pZA50. Anyone skilled in the art will appreciate that this invention is not limited to the aforementioned two genes because this gene transfer methodology, as is true with all gene transfer methodologies is not limited by a particular DNA sequence. The stable transformants were recovered by the method shown in FIG. 5.

Transformed protoplasts were maintained for 4 weeks on nonselective medium before randomly picked 2-mm microcalli were moved to selective medium for tests of nptII expression (neomycin resistance) or to microtiter dishes for histochemical tests of GUS enzymatic activity (26). When randomly selected microcalli were transferred after seven days to 200ug/ml Kanamycin medium, 23% of these microcalli showed moderate to rapid growth on the antibiotic. Kanamycin resistant (Kan®) nptII-containing microcalli were recovered from 23% of all microcalli showing moderate to rapid growth on 200 ug/ml kanamycin after 7 d. GUS activity was observed in 9% of randomly picked microcalli.

Stringent proof of stable transformation resulting from integration of a foreign gene into host DNA requires molecular evidence for integration of the transfecting gene and biochemical demonstration of occurrence of the expected gene product. Both of these criteria for the two donor genes used have been satisfied. After restriction with BamHI and hybridization with a 1.0 kb BamHI nptII probe, genomic DNA isolated from Kan® microcalli after 2PC transfection revealed the characteristic 1.0 kb nptII-containing fragment. Restriction of two of these Kan® genomic DNAs with EcoRV, an enzyme which cuts at one site within the transfecting plasmid and at several external sites within the maize genome, reveals several patterns of bands hybridizing to the BamHI probe (FIG. 6, lanes c and d). This indicates nptII integration at different independent genomic sites, at least 4 in each of the two examples shown. Neomycin phosphotransferase activity in several Kan® transformants was assayed by the TLC method of Cabanes-Bastos et al.(23) (FIG. 7). Lanes 2, 3, 4 and 10 show evidence of phosphorylated kanamycin in extracts of 3, 2PC-transformed Kan® colonies. After transformation with pZA50, genomic DNA of one GUS-positive transformant was tested for GUS gene integration (FIG. 8, lane BMS). In this instance PstI and EcoRI, restriction enzymes which digest at the 5' and 3' ends of the GUS cassette, were used to digest genomic DNA which was then probed with the homologous 2.85 kb PstI-EcoRI region obtained from pZA50. A positive hybridization signal was obtained in a 2.85 kb genomic DNA band. As noted above, the GUS gene was expressed in 10/114 microcalli tested.

Gene transfer by the 2PC method was also tested in protoplasts derived from tobacco line NT1 (27). After transfer of pZA50, 100 colonies were grown on nonselective medium as described for maize protoplasts in FIG. 5. GUS activity was demonstrated in 24/100 stable transformants and one of these was tested for the integration of the GUS cassette (gene and regulatory regions) (FIG. 8, lane NT1). The genomic DNA of this transformant included the characteristic 2.85 kb GUS-containing band. This is evidence of the widespread applicability of the 2PC method to all cells including tobacco and corn protoplasts.

It will be understood that the embodiments described herein are merely exemplary and that a person skilled in the art may make any variations and modifications without departing from the spirit and scope of the claimed invention. All such modifications and variations are intended to be included in the scope of the invention, as defined in the appended claims.

TABLE 1

Chloramphenicol acetyl transferase activity per 100 mg protein in BMS-M protoplasts after transformation with pCaMNI,CN by cationic methods.

| Treatment | DNA concentration (ug) | | | | | | |
|---|---|---|---|---|---|---|---|
| | 0 | 0.1 | 0.5 | 5 | 10 | 20 | 50 |
| PB | 0.1$^{a,b}$ | 0.2 | 1.0 | 3.4 | 4.6 | 6.2 | 1.4 |
| LF | 0.1 | 4.9 | 10.7 | 2.1 | 1.6 | 3.6 | 3.0 |
| 2PC: Observed values | 0.2 | 4.6 | 4.6 | 12.1 | 38.5 | 49.4 | 1.9 |
| Expected additive effect | — | 5.1 | 11.7 | 5.5 | 7.2 | 9.8 | 4.4 |
| Fold increase | — | — | — | 2.2 | 5.3 | 5.1 | — |
| No. of trials showing positive synergistic response | — | — | ⅓ | 2/2 | 2/2 | 3/3 | ⅓ |

$^a$CAT activity is expressed as the % of $^{14}$C chlorampheicol converted to acetylated products (1- and 3- monoacetyl chloramphenicol).
$^b$Average values from 2–3 independent experiments.

TABLE 2

Chloramphenicol acetyl transferase activity in total lysate from 2 × 10$^6$BMS-M protoplast samples after cationic transfection of pCaMVI,CN.

| Treatment | DNA concentration (ug) | | | | |
|---|---|---|---|---|---|
| | 0.5 | 5 | 10 | 20 | 50 |
| PB | 1.0$^{a,b}$ | 4.8 | 9.8 | 8.22 | 1.58 |
| LF | 12.2 | 2.7 | 2.9 | 5.75 | 8.6 |
| 2PC: Observed values | 8.3 | 29.0 | 64.6 | 54.3 | 36.9 |
| Expected additive effect | 13.2 | 7.5 | 12.7 | 14.0 | 10.2 |
| Fold increase | — | 3.8 | 5.1 | 3.9 | 3.6 |
| No. of trials showing positive synergisitic response | ⅓ | ⅓ | 3/3 | 3/3 | ⅓ |

$^a$CAT activity is expressed as in Table 1.
$^b$Average values from 3–4 independent experiments.

TABLE 3

Transient expressions of chloramphenicol acetyl transferase activity[a] after direct gene transfer by cationic treatments to protoplasts derived from $F_1A188/Mu^2 60,B70$ embryogenic callus.

| Experiment | Treatment | | |
|---|---|---|---|
| | PB | LF | 2PC |
| 1 | — | 0.21 | 5.01 |
| 2 | .25[a] | .2 | 10.8 |
| 3 | — | .07 | 1.35 |

[a]CAT activity is expressed as described in Table 1.

BIBLIOGRAPHY

1. Shimamoto, K., Terada, R., Izawa, T. & Fujimoto, H. Nature 338:274–276. (1989)
2. Rhodes, C. A., Pierce, D. A., Mettler, I. J., Mascarenhas, D. & Detmer, J. J. Science 240:204–207. (1988)
3. Klein, T. M., Fromm, M., Weissinger, A., Tomes, D., Schauf, S., Sletten, M., & Sanford, J. C. Proc. Natl. Acad. Sci. USA 85:4305–4309. (1988)
4. De la Pena, A., Lorz, H. & Schell, J. Nature 325:274–276. (1987)
5. Shillito, R. D., Carswell, G. K., Johnson, C. M., Di Maio, J. J., & Harms, C. T. Biotechnology 7:581–588. (1989)
6. Prioli, L. M. & Sondahl, M. R. Biotechnology 7:589–594. (1989)
7. Fromm, M., Taylor, L. P. & Walbot, V. Nature 319:791–793. (1986)
8. Antonelli, N. M., & Stadler, J. J. Genet & Breeding 43: 113–121. (1989)
9. Antonelli, N. M. & Stadler, J. Manuscript. (1989)
10. Felgner, P. L., Gadek, T. R., Holm, M., Roman, R., Chan, H. V., Wenz, M., Northrop, J. P., Ringold, G. M., & Danielsen, M. Proc. Natl. Acad. Sci. USA 4:7413–7417. (1987)
11. Murashige, T. & Skoog, F. Physiol. Plant. 15:473–497. (1962)
12. Somers, D. A., Birnberg, P. R., Petersen, W. L. & Brenner, M. L. Plant Sci. 53:249–256. (1988)
13. Green, C. E. & Phillips, R. L. Crop Sci. 15:117–121. (1975)
14. Chu, C. C., Wang, C. C., Sun, C. S., Hsu, C., Yin, K. C., Cu, C. Y. and Bi, F. Y. Sci. Sinica 18:659–668. (1975)
15. Widholm, J. M. Stain Technol. 47:189–190. (1972)
16. Chourey, P. S., Zurawski, D. B. Theor. Appl. Genet. 59:341–344. (1981)
17. Planckaert, F. & Walbot, V. Personal communication. (1988)
18. Callis, J., Fromm, M., Walbot, V. Gene Dev. 1:1183–1200. (1987)
19. Zhou, J. H. Personal communication. (1989)
20. Maniatis, T., Fritsch, E. F., Sambrock, J. Cold Spring Harbor Laboratory, Cold Spring Harbor, N.Y. (1982)
21. Gorman, C. M., Moffat, L. F., Howard, B. H. Mol. Cell Biol. 2:1044–1051. (1982)
22. Bradford, M. M. Anal. Biochem. 72:248–254. (1976)
23. Cabanes-Bastos, E., Day, A. G., & Lichtenstein, C. P. Gene 77:169–176. (1989)
24. Mettler, I. J. Plant Mol. Biol. Rep. 5:346–349. (1987)
25. Southern, E. M., J. Mol. Biol. 98:503–517. (1975)
26. Jefferson, R. A., Kavanaugh, T. A., & Bevan, M. W. Embo J. 6:3901–3907. (1987)
27. Paszty, C. & Lurquin, P. F. BioTechniques 5:716–718. (1987)
28. Wood, K. R. "Tissue Culture Methods in Phytopathology I-Viruses" in *Plant Cell Culture A Practical Approach, Dixon*, R. A. ed. IRL Press (1985)
29. Shillito, R. D., Saul, M. W., Paszkowski, J., Muller, M., Potrybus, I. Biotecnology 3:1099–1103. (1985)
30. Pollard, J. W., Sollustio, S. and Stanley, P. Somatic Cell and Mol. Genet. 12:237–244. (1986)

What is claimed is:

1. A method for transforming a cell comprising
   treating for a predetermined time a host cell with a solution of a polycation compound to form a cell polycation complex;
   treating DNA nonnative to said host cell with a suspension of cationic liposomes to form a DNA liposome complex at a predetermined DNA/lipid ratio;
   combining said DNA liposome complex with said cell polycation complex thereby transforming said host cell with said nonnative DNA.

2. The method of claim 1 wherein said cell has as its outer boundary a membrane.

3. The method of claim 1 wherein said cell reacts with said polycation compound solution for between one minute and three hours prior to combining said polycation compound solution with said DNA cationic liposome complex.

4. The method of claim 1 wherein said cell is a protoplast which reacts with said polycation compound solution for substantially one quarter of an hour prior to combining with said DNA cationic liposome complex.

5. The method of claim 1 wherein said polycation compound is a salt of hexadimethrine.

6. The method of claim 1 wherein said polycation compound is selected from salts of the group consisting of poly-L-ornithine, poly-L-arginine, poly-L-lysine, poly-D-lysine and polyethleneimine.

7. The method of claim 1 wherein said cell is a monocotyledonous plant cell.

8. The method of claim 1 wherein said cell is from a maize cell.

9. The method of claim 1 wherein said plant cell is a dicotyledonous cell.

10. The method of claim 1 wherein said cationic lipid comprises a salt of a synthetic cationic lipid designated N-[1-(2,3-dioleyloxy)propyl]N,N,N trimethylammonium.

11. The method of claim 1 wherein said cationic liposomes interact in the presence of said DNA to form liposome DNA aggregates.

12. The method of claim 1 wherein said DNA is treated with said suspension of cationic liposomes in a DNA/lipid ratio between 1:2.5 and 1:1.25.

13. The method of claim 1 wherein said DNA is treated with said suspension of cationic liposomes to maximize said DNA/lipid ratio.

* * * * *

UNITED STATES PATENT AND TRADEMARK OFFICE
CERTIFICATE OF CORRECTION

PATENT NO. : 5,286,634
DATED : February 15, 1994
INVENTOR(S) : Stadler et al.

It is certified that error appears in the above-indentified patent and that said Letters Patent is hereby corrected as shown below:

Column 2, line 11, "Aqrobacterium-mediated" should read
--Agrobacterium-mediated--.
Column 2, lines 25 and 26, "Aorobacterium-mediated" should read
--Agrobacterium-mediated--.
Column 2, line 29, "Aqrobacterium" should read
--Agrobacterium--.
Column 4, line 37, "2PC-" should read --2PC-treated--.
Column 5, line 3, "7 d" should read --7d--.
Column 5, line 25, "phosporylated" should read
--phosphorylated--.
Column 5, line 30, "structure" should read --structural--.
Column 10, line 51, "BamHI" should read --BamH1--.
Column 15, line 47, "BamHI" should read --BamH1--.
Column 15, line 48, "BamHI" should read --BamH1--.
Column 15, line 55, "BamHI" should read --BamH1--.
Column 16, line 45, "chlorampheicol" should read
--chloramphenicol--.
Column 17, line 41, "4:7413-7417" should read
--84:7413-7417--.
Column 18, line 46, "polyethleneimine" should read
--polyethyleneimine--.

UNITED STATES PATENT AND TRADEMARK OFFICE
CERTIFICATE OF CORRECTION

PATENT NO. : 5,286,634
DATED : February 15, 1994
INVENTOR(S) : Stadler et al.

It is certified that error appears in the above-indentified patent and that said Letters Patent is hereby corrected as shown below:

Column 7, line 63, "polyethleneimine" should read --polyethyleneimine--.

Signed and Sealed this

Twenty-fourth Day of September, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,286,634
DATED : February 15, 1994
INVENTOR(S) : Stadler et al.

It is certified that error appears in the above-identified patent and that said Letters Patent is hereby corrected as shown below:

On the cover page, the Assignee should be:

Iowa State University Research Foundation, Inc., Ames, Iowa

Signed and Sealed this

Twenty-fifth Day of March, 1997

Attest:

BRUCE LEHMAN

Attesting Officer

Commissioner of Patents and Trademarks